US009469925B2

(12) United States Patent
McMahon et al.

(10) Patent No.: US 9,469,925 B2
(45) Date of Patent: Oct. 18, 2016

(54) STENT DESIGNS AND METHODS OF MANUFACTURE

(71) Applicant: Boston Scientific Scimed, Inc., Maple Grove, MN (US)

(72) Inventors: Shane McMahon, Co Galway (IE); Thomas Martin Keating, Galway (IE); Conor Ryan, County Clare (IE); John Allen Hingston, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 106 days.

(21) Appl. No.: 14/455,320

(22) Filed: Aug. 8, 2014

(65) Prior Publication Data

US 2015/0045874 A1 Feb. 12, 2015

Related U.S. Application Data

(60) Provisional application No. 61/864,242, filed on Aug. 9, 2013.

(51) Int. Cl.
*D04C 3/48* (2006.01)
*D04C 3/12* (2006.01)
(Continued)

(52) U.S. Cl.
CPC . *D04C 3/48* (2013.01); *A61F 2/88* (2013.01); *A61F 2/90* (2013.01); *A61L 31/10* (2013.01); *B29C 53/36* (2013.01); *B29C 65/08* (2013.01); *B29C 65/16* (2013.01); *B29C 66/5221* (2013.01); *D04C 3/12* (2013.01); *A61F 2220/0033* (2013.01);
(Continued)

(58) Field of Classification Search
CPC ............. A61F 2/90; D04C 3/12; D04C 3/48; D04C 1/12
See application file for complete search history.

(56) References Cited

U.S. PATENT DOCUMENTS

| 4,655,771 A | 4/1987 | Wallsten |
| 6,159,239 A | 12/2000 | Greenhalgh |

(Continued)

FOREIGN PATENT DOCUMENTS

| EP | 1813231 A1 | 8/2007 |
| EP | 2301486 A1 | 3/2011 |

(Continued)

OTHER PUBLICATIONS

PCT International Search Report; PCT International Application No. PCT/US2014/050372 (Filing Date: Aug. 8, 2014); mailed Dec. 19, 2014; 5 pages.

(Continued)

*Primary Examiner* — Shaun R Hurley
(74) *Attorney, Agent, or Firm* — Seager, Tufte & Wickhem, LLP

(57) ABSTRACT

Embodiments disclosed include a woven stent and a method of manufacturing a woven stent that includes a plurality of first members and a plurality of second members forming a braided configuration; wherein each of the first members includes a first body portion, a first end unjoined portion, and a first end bent portion; wherein each of the second members includes a first end overlap portion extending alongside the first end unjoined portion. The woven stent may further includes a coating that encapsulates the first end unjoined portions and the first end overlap portions and/or the first end unjoined portions may be laser joined or ultrasonic joined to the first end overlap portions.

11 Claims, 10 Drawing Sheets

(51) Int. Cl.
*A61F 2/88* (2006.01)
*A61L 31/10* (2006.01)
*B29C 53/36* (2006.01)
*B29C 65/08* (2006.01)
*B29C 65/16* (2006.01)
*B29C 65/00* (2006.01)
*A61F 2/90* (2013.01)
*B29K 67/00* (2006.01)

(52) U.S. Cl.
CPC . *A61F 2230/0069* (2013.01); *A61F 2240/001* (2013.01); *A61F 2250/0039* (2013.01); *B29K 2067/003* (2013.01); *B29K 2995/006* (2013.01); *B29K 2995/0056* (2013.01)

(56) References Cited

U.S. PATENT DOCUMENTS

| | | | | |
|---|---|---|---|---|
| 7,462,192 B2* | 12/2008 | Norton | ............... | A61F 2/90 264/103 |
| 7,857,844 B2* | 12/2010 | Norton | ............... | A61F 2/90 623/1.53 |
| 8,052,739 B2 | 11/2011 | Pulnev et al. | | |
| 8,114,147 B2* | 2/2012 | Wood | ............... | A61F 2/90 623/1.15 |
| 8,151,682 B2* | 4/2012 | Lilburn | ............... | D04C 1/06 87/9 |
| 8,449,599 B2* | 5/2013 | Chau | ............... | A61F 2/2418 623/1.24 |
| 2003/0040771 A1* | 2/2003 | Hyodoh | ............... | A61F 2/90 606/200 |
| 2005/0256563 A1* | 11/2005 | Clerc | ............... | A61F 2/90 623/1.16 |
| 2009/0198315 A1* | 8/2009 | Boudjemline | ............ | A61F 2/90 623/1.2 |
| 2011/0172763 A1 | 7/2011 | Ndondo-Lay | | |
| 2012/0259404 A1 | 10/2012 | Tieu et al. | | |
| 2012/0265294 A1 | 10/2012 | Nishigishi | | |
| 2012/0330398 A1 | 12/2012 | Hyodoh et al. | | |

FOREIGN PATENT DOCUMENTS

| | | |
|---|---|---|
| EP | 2510907 A1 | 10/2012 |
| EP | 2510907 B1 | 8/2014 |
| WO | 2012082440 A1 | 6/2012 |

OTHER PUBLICATIONS

PCT Invitation to Pay Additional Fees and, Where Applicable, Protest Fee; PCT International Application No. PCT/US2014/050372 (Filing Date: Aug. 8. 2014); mailed Oct. 9, 2014; 4 pages.
PCT Written Opinion of the International Searching Authority; PCT International Application No. PCT/US2014/050372 (Filing Date: Aug. 8, 2014); mailed Dec. 19, 2014; 7 pages.

* cited by examiner

STENT DESIGNS AND METHODS OF MANUFACTURE

CROSS REFERENCE TO RELATED APPLICATIONS

This application claims the benefit of and priority to U.S. Provisional Patent Application No. 61/864,242, filed Aug. 9, 2013.

FIELD

The present disclosure relates to the field of woven stent designs and methods of manufacturing stents including unjoined portions and overlap portions secured by a coating and/or secured by laser joining.

BACKGROUND

A stent is a medical device introduced into a body lumen and is well known in the art. A stent may be delivered in an unexpanded state to a desired location in a bodily lumen and then expanded by an internal radial force. Stents, grafts, stent-grafts, vena cava filters, expandable frameworks, and similar implantable medical devices, collectively referred to hereinafter as stents, have included radially expandable endoprostheses, which have been used as intravascular implants capable of being implanted transluminally.

Esophageal stents have been used to treat patients suffering from a range of malignant and non-malignant diseases. Most commonly, esophageal stents have been associated with the treatment of esophageal cancers. Esophageal stents have also been used to reduce symptoms resulting from non-esophageal tumors that grow to obstruct the esophagus and to treat benign esophageal disorders, including but not limited to refractory strictures, fistulas and perforations. In each of these cases, esophageal stents may provide mechanical support to the esophageal wall and may maintain luminal patency.

Metallic stents have been used in applications including cancerous strictures and treatment of refractory benign, esophageal, biliary, colonic, and duodenal strictures, and "bridge to recovery" or "bridge to surgery" applications for a suitable time period. Polymeric stents have also been used to treat these indications and have had an added advantage of allowing stent removability. In at least some stent applications, polymeric stents have offered one or more advantages over metallic stents, the advantages including reduced tissue reaction, reduced or eliminated radiation scatter, and/or improved removability.

Some stents have included one or more longitudinal members (e.g., wires, filaments, etc.) that are braided in a pattern. Various braided stents are disclosed by, for example, Wallsten (U.S. Pat. No. 4,655,771), Greenhalgh (U.S. Pat. No. 6,159,239), Tieu et al. (U.S. Pat. PGPUB 2012/0259404), Pulnev et al. (U.S. Pat. No. 8,052,739), and Nishigishi (U.S. Pat. PGPUB 2012/0265294).

In order to, for example, reduce tissue ingrowth, stents have been covered with a coating (e.g., made of a polymer, etc.) to create a physical barrier between the lumen of the stent and the wall of a body lumen (e.g., esophagus, etc.).

Stents having closed loop ends have been employed to provide, for example, atraumatic stent ends for improved patient comfort and reduced recovery time. Closed loop stent ends have also aided removability of a stent by allowing the addition of a suture (e.g., by weaving the suture through one or more closed loop ends, etc.) to the stent which can be used by an operator (e.g., a physician, etc.) to remove the stent if desired.

Lasers (Light Amplification by Stimulated Emission of Radiation) have been used in a variety of applications to deliver concentrated light energy to a work piece, wherein the light energy may be absorbed and converted to thermal energy in order to, for example, heat the work piece. Ultrasonic energy has been used in a variety of applications to deliver sound energy (e.g., concentrated and/or focused sound energy) to a work piece, wherein the sound energy may be absorbed and converted to thermal energy in order to, for example, heat the work piece.

Improved stents with, for example, improved ability to secure loose ends and/or improved retrievability are desired. Methods of manufacturing stents having improved ability to secure loose ends are desired.

Without limiting the scope of the present disclosure, a brief summary of some of the claimed embodiments is provided below. Additional details of the summarized embodiments and/or additional embodiments can be found in the detailed description.

All US patents and applications and all other published documents mentioned anywhere in this application are incorporated herein by reference, each in its entirety.

SUMMARY

One or more aspects of the present disclosure relates to a woven stent that includes a tubular structure having a first end and a second end. The tubular structure defines a lumen extending from the first end to the second end and defines a central axis extending through the lumen in a longitudinal direction of the tubular structure. The tubular structure includes a plurality of first members and a plurality of second members. In one or more embodiments, the first members and the second members form a braided configuration. In at least one embodiment, each of the first members includes a first body portion extending in a first helical direction around the central axis, a first end unjoined portion extending in a second helical direction around the central axis, wherein the second helical direction is opposite of the first helical direction; and a first end bent portion connecting the body portion to the first end unjoined portion at the first end. In the present disclosure, a "bent portion" (e.g., first end bent portion, second end bent portion) is a portion of a member connecting a right-handed helical portion of the member with a left-handed helical portion of the member. In one or more embodiments, each of the second members includes a first end overlap portion extending alongside the first end unjoined portion of a first member and a second body portion extending from the first end overlap portion in the second helical direction around the central axis toward the second end. In one or more embodiments, the tubular structure further includes a coating (e.g., a first end coating, etc.) that encapsulates the first end unjoined portions of the first members and the first end overlap portions of the second members.

One or more aspects of the present disclosure relates to a method for manufacturing a stent. The method includes forming a tubular structure having a first end and a second end, wherein the tubular structure defines a lumen extending from the first end to the second end and defines a central axis extending through the lumen in a longitudinal direction of the tubular structure. Forming the tubular structure includes braiding a plurality of first members with a plurality of second members to form a braided configuration. Forming the tubular structure may also include bending at least one of the plurality of first members to form a first end bent portion connecting a first body portion arranged to extend in a first helical direction to a first end unjoined portion at the first end, the first end unjoined portion arranged to extend in a second helical direction around the central axis, wherein the second helical direction is opposite of the first helical direction. Forming the tubular structure may also include disposing at least one of the plurality of second members such that the second member includes a first end overlap portion extending alongside the first end unjoined portion of a first member and such that a second body portion extends from the first end overlap portion in the second helical direction around the central axis and toward the second end. The method further includes coating at least a portion of the first end such that the coating encapsulates the first end unjoined portion of the at least one first member and the first end overlap portion of the at least one second member.

One or more aspects of the present disclosure relates to a method for manufacturing a stent. The method includes forming a tubular structure having a first end and a second end. The tubular structure also defines a lumen extending from the first end to the second end. The tubular structure includes a plurality of first members and a plurality of second members. The method includes contacting a first end unjoined portion of a first member with a first end overlap portion of a second member, wherein the first end overlap portion is parallel to the first end unjoined portion and wherein a line of contact is formed between the first end unjoined portion and the first end overlap portion. The method includes joining the first end unjoined portion and the first end overlap portion, wherein joining includes directing laser energy at the line of contact to heat the first end unjoined portion and the first end overlap portion at the line of contact to a joining temperature for a time sufficient to form a bond upon cooling and allowing the line of contact to cool, thereby forming a bond between the first end unjoined portion and the first end overlap portion.

DETAILED DESCRIPTION

Figure 1A:
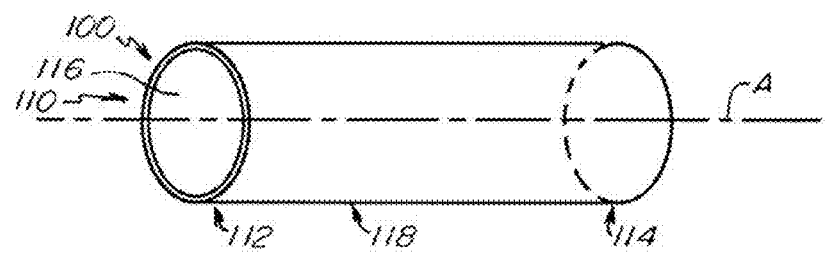
FIG. 1A depicts a schematic of a woven stent according to at least one embodiment the present disclosure.

While the subject matter of the present disclosure can be embodied in many different forms, specific embodiments are described in detail herein. This description is an exemplification of the principles of the present disclosure and is not intended to limit the present disclosure to the particular embodiments illustrated.

For the purposes of this disclosure, like reference numerals in the figures shall refer to like features unless otherwise indicated.

Various aspects of the present disclosure are depicted in the figures. Elements depicted in one figure can be combined with and/or substituted for elements depicted in another figure as desired.

The terms proximal and distal, described in relation to various devices, apparatuses, and components as discussed in the subsequent text of the present disclosure, are referred with a point of reference. The point of reference, as used in this description, is a perspective of an operator. The operator can be a surgeon, a physician, a nurse, a doctor, a technician, and the like, who can perform the procedure of delivery and placement of the disclosed system/device into a patient's body as described in the present disclosure. The term proximal refers to an area or portion that is closer or closest to the operator during a placement procedure. The term distal refers to an area or portion that is further or farthest from the operator.

Referring now to FIG. 1A, a schematic of stent 100 (e.g., woven stent) is shown, having a generally tubular structure 110 having a first end 112 and a second end 114. The tubular structure 110 defines a lumen 116 that extends from the first end 112 to the second end 114. The tubular structure 110 also defines a central axis A extending through the lumen 116 in a longitudinal direction of the tubular structure 110.

In one or more embodiments, as shown in FIG. 1A, the tubular structure 110 of stent 100 may be cylindrical, having a uniform diameter along its entire length (e.g., first end 112 has a diameter and second end 114 has a diameter that is the same as the diameter of the first end 112). Although not shown, the tubular structure 110 may take any of a wide variety of geometric or nongeometric shapes provided that the tubular structure defines a lumen extending from the first end to the second end.

In one or more embodiments, the tubular structure 110 may have a variable diameter along its length and may include one or more cylindrical portions separated by diameter transition (e.g., expanding, contracting) portions (e.g., cones, frustoconical portions, etc.). The diameter transition portion may have any suitable length. In one or more embodiments, a tubular structure 110 having multiple diameters along its length may include a cylindrical first end 112 and a cylindrical second end 114, wherein the diameter of the first end 112 may be the same as or different from the diameter of the second end 114. In one or more embodiments, disposed between the first end 112 and the second end 114 may be a medial portion 118 (e.g., a cylindrical medial portion) having a diameter that is the same as or different from one or both of the respective diameters of the first end 112 and the second end 114. In some embodiments, the medial portion 118 has a diameter that is smaller than the respective diameters of the first end 112 and the second end 114. In one or more embodiments in which the tubular structure 110 has a variable diameter along its length, the tubular structure 110 may include all concentric portions (e.g., central axis A is a straight line defining the center point of the tubular structure along the tubular structures longitudinal length) or may include one or more eccentric portions (e.g., the center point of an eccentric portion does not align with the center point of one or more other portions of the tubular structure).

In the present disclosure, the stent may have any dimensions (e.g., longitudinal length, translongitudinal length (e.g., diameter, etc.)) suitable for the application and implantation site in which the stent is intended.

Figure 1B:
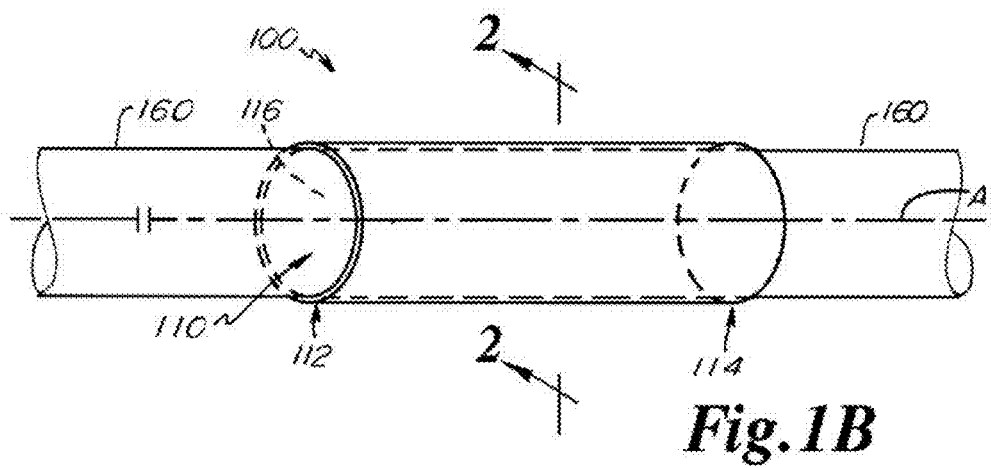
FIG. 1B depicts a schematic of a woven stent according to at least one embodiment the present disclosure, wherein the stent is disposed on a mandrel.

In FIG. 1B, a schematic is provided showing stent 100 mounted on a mandrel 160. As discussed herein, in one or more embodiments, one or more of the manufacturing steps to form stent 100 may include a mandrel 160.

Figure 2:
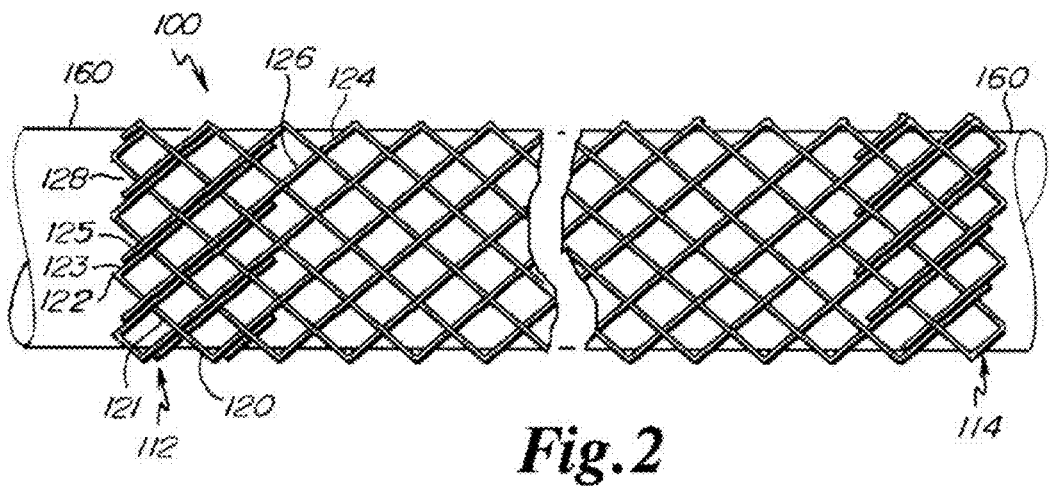
FIG. 2 depicts a schematic of a woven stent of FIG. 1B showing additional detail regarding a plurality of first members and a plurality of second members in accordance with at least one embodiment of the present disclosure, wherein the stent is disposed on a mandrel.
Figure 3A:
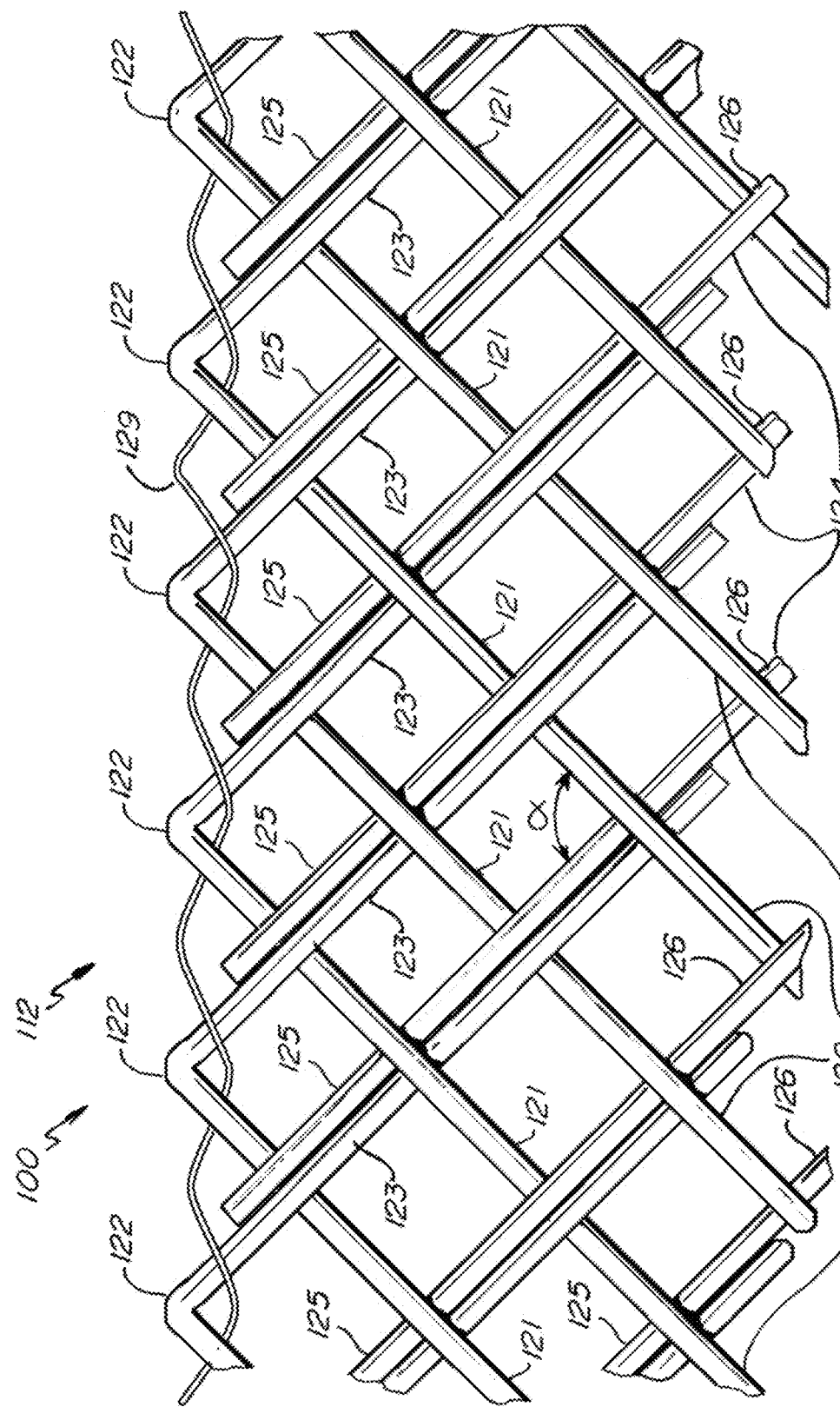
FIG. 3A depicts an enlarged portion of the first end of the woven stent of FIG. 2 in accordance with at least one embodiment of the present disclosure.

FIG. 2 depicts a more detailed side (e.g., translongitudinal) view of stent 100 of FIG. 1B, showing the one or more members (e.g., longitudinal members) that form the tubular structure 110. FIG. 3A shows an enlarged view of a portion of first end 112 of tubular structure 110 of stent 100. In one or more embodiments, as shown in FIGS. 2 and 3A, tubular structure 110 includes a plurality of first members 120 and a plurality of second members 124.

In at least one embodiment, each of the first members 120 includes a first body portion 121 extending in a first helical direction around the central axis A (FIG. 1A), a first end unjoined portion 123 extending in a second helical direction around the central axis A, and a first end bent portion 122 connecting the body portion 121 to the first end unjoined portion 123 at the first end 112. In one or more embodiments, the second helical direction of the first end unjoined portion 123 is opposite of the first helical direction of the first body portion 121. In other words, one of the first end unjoined portion and the first body portion extends in a right-handed helical around axis A and the other extends in a left-handed helical around axis A. In the present disclosure, "helical" refers to a path (e.g., a winding path) that simultaneously extends both around a central axis and in a longitudinal direction along the central axis and includes winding paths of constant or variable diameter along the central axis and/or constant or varying pitch (length along the central axis corresponding to extending around the central axis by 360 degrees).

As shown in FIG. 3A, first members 120 and second members 124 intersect at an angle α that opens in the direction of the first end 112. In one or more embodiments, angle α may be obtuse. In one or more embodiments, angle α may be acute. In one or more embodiments, angle α may be in the range of from 45 degrees to 135 degrees.

As shown in FIG. 3A, in one or more embodiments, each of the second members 124 includes a first end overlap portion 125 extending alongside the first end unjoined portion 123 of a first member 120. In one or more embodiments, each of the second members 124 also includes a second body portion 126 extending from the first end overlap portion 125 in the second helical direction around the central axis A toward the second end 114.

In one or more embodiments, the plurality of first members includes two or more first members (e.g., four or more first members, 6 or more first members, 8 or more first members, 12 or more first members, 16 or more first members, 18 or more first members, 24 or more first members, or 36 or more first members). In one or more embodiments, the plurality of second members includes two or more second members (e.g., four or more second members, 6 or more second members, 8 or more second members, 12 or more second members, 16 or more second members, 18 or more second members, 24 or more second members, or 36 or more second members). In one or more embodiments, a plurality of first members may include 18 wires or 18 filaments and a plurality of second members may include 18 wires or 18 filaments. Each of the plurality of first members and plurality of second members may include a combination of a quantity of wires and a quantity of filaments. In one or more embodiments, the plurality of first members includes the same number of first members as the plurality of second members includes of the second members.

In the present disclosure, each of the plurality of first members and the plurality of second members may be in the form of a wire or a filament. In one or more embodiments, a wire may include a single wire or may include a plurality of wires braided together (e.g., a cable, etc.). In one or more embodiments, a filament may be a monofilament or may include more than one filament bound together (e.g., braided) in a longitudinal member. A wire may be formed from any of a wide variety of materials and may include any suitable biocompatible materials including, but not limited to, one or more polymers, one or more metals (e.g., metallic, an alloy, a composite, etc.), or combinations of polymer(s) and metal(s). Examples of suitable materials for a wire or a filament include biodegradable materials that are also biocompatible. A biodegradable material, as used herein, is meant to refer to a material that will undergo breakdown or decomposition into harmless compounds as a part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. In one or more embodiments, a wire may include nickel, titanium, iron, cobalt, and/or chromium. In one or more embodiments, exemplary materials for forming a wire or filament may include, but are not limited to stainless steel, titanium, tantalum, platinum, tungsten, gold, and alloys of any of the above-mentioned metals, including, but not limited to nickel titanium (e.g., nitinol alloy), cobalt chrome (e.g., alloys including cobalt and chromium, such as Elgiloy®, Phynox®, and MP35N®), and other medical grade biocompatible compositions. A filament may include any of a wide variety of polymers known in the art. For example, a filament (e.g., a polymeric monofilament, etc.) may include a thermoplastic and/or a bioabsorbable polymer. In one or more embodiments, a filament may include one or more of polyethylene terephthalate (PET), polylactic acid (PLA), and polyglycolic acid (PGA). In one or more embodiments, a filament may be formed entirely from or consist essentially of one or more of polyethylene terephthalate (PET), polylactic acid (PLA), and polyglycolic acid (PGA). In one or more embodiments, a wire or filament may include polyester and polycarbonate copolymers.

In the present disclosure, each of the plurality of first members 120 and each of the plurality of second members 124 may have any dimensions (e.g., longitudinal length, translongitudinal length (e.g., diameter, cross-sectional dimension, etc.)) suitable for forming stent 100, depending on the application and implantation site in which stent 100 is intended. In one or more embodiments, the length of the first members and second members is sufficient to extend in a helical direction around the central axis A along the length of stent 100 and terminating at, for example, an overlap portion or a corresponding unjoined portion. In one or more embodiments, the length of each of the first members 120 is the same as the length of each of the second members 124. The diameter (or other cross-sectional dimension) of the first members 120 and/or second members 124 may be any length suitable to provide stent 100 with the desired structural characteristics, depending on the application and implantation site intended.

In one or more embodiments, as shown in FIG. 2 (not shown in FIG. 3A), the tubular structure further includes a coating 128 (e.g., a first end coating) that encapsulates the first end unjoined portions 123 of the first members 120 and the first end overlap portions 125 of the second members 124.

A coating of the present disclosure may include any of a wide variety of suitable materials, such as a polymer. In one or more embodiments, the coating may include a silicone polymer (e.g. medical grade silicone). For example, a medical grade silicone may be commercially available from E.I. DuPont DeNemours & Co. (Wilmington, Del.), NuSil Technology LLC (Carpinteria, Calif.), and/or GE Polymers. In one or more embodiments, the coating may include more than one polymer (e.g., a mixture, blend, block copolymer, random copolymer, graft copolymer, etc.). One of skill in the art will be able to envision and/or select one or more suitable coating materials depending on the intended application and/or implantation site of stent 100. In one or more embodiments, the coating includes a biocompatible polymer. In one or more embodiments, the coating includes a bioabsorbable polymer such as a bioabsorbable elastomer. In one or more embodiments, a coating may include one or more therapeutic agents (e.g., embedded therein, coated thereon, etc.). Some exemplary therapeutic agents may include, but are not limited to, angiopeptin, paclitaxel, everolimus, dexamethasone, methyl prednisolone, zotarolimus, estradiol, and batimastat. Other exemplary therapeutic agents may include, but are not limited to, those disclosed by Ndondo-Lay (U.S. Pat. PGPUB 2011/0172763).

In one or more embodiments, the first members 120 and the second members 124 form a braided configuration, as shown in FIG. 3A. In one or more embodiments, the braided configuration includes one or both of the first members 120 and second members 124 being configured in a repeating over-under-over-under braided configuration. In the present disclosure, with regard to braided configurations, "over" and "under" are meant to relate positions of two objects in relation to proximity to axis A. For example, with regard to braided configurations, a first article extending "over" a second article is intended to mean that the first article intersects with the second article such that the first article is further from axis A than the second article at the point of intersection. Similarly, with regard to braided configurations, a first article extending "under" a second article is intended to mean that the first article intersects with the second article such that the first article is closer to axis A than the second article at the point of intersection.

A braided configuration of the present disclosure may include any of a wide variety of braid patterns (e.g., over-over-under, over-over-under-under, etc.) that form cells. In one or more embodiments, as shown in FIG. 3A, a first end unjoined portion 123 of a first member 120 extends over and under the same members as the first end overlap portion 125 (of a second member 124) that extends alongside the first end unjoined portion 123. In FIG. 3, each of the first end unjoined portions 123 is paired with a corresponding first end overlap portion 125, wherein both of the first end unjoined portion and the corresponding first end overlap portion 125 extend over and under the same members.

In one or more embodiments, the plurality of first members and the plurality of second members form a plurality of cells bound on two sides by adjacent members extending in a right-handed helical direction and bound on two sides by adjacent members extending in a left-handed helical direction. In one or more embodiments, the cells are four sided (e.g., quadrilaterals, parallelograms, rhombuses, diamonds, etc.). In one or more embodiments, a first end unjoined portion 123 of a first member 120 and a corresponding first end overlap portion 125 of a second member 124 may combine to form a single side of a particular cell. For example, each cell that includes a first end bent portion 122 includes at least one side that includes a first end unjoined portion 123 and a first end overlap portion 125. Some cells may include two or more sides, each of which includes a first end unjoined portion 123 and a first end overlap portion 125.

In one or more embodiments, the distance from a terminal end of at least one first end unjoined portion 123 to a terminal end of the corresponding first end overlap portion may be selected in combination with a coating material and thickness such that the first end unjoined portion and the first end overlap portion remain encapsulated within coating 128 when a suture 129 is woven through at least one cell (e.g., a cell at a terminal end of a stent) and pulled with a force of at least 3.3 lbf. In one or more embodiments, the distance from a terminal end of at least one first end unjoined portion 123 to a terminal end of the corresponding first end overlap portion is at least one diamond (e.g., at least two diamonds, at least three diamonds, at least four diamonds, at least five diamonds, etc.). In the present disclosure, the length of a "diamond" is the length of one side of a cell in the direction the length is being measured.

In one or more embodiments, the length of at least one first end unjoined portion 123 of a first member 120 is sufficient to cross at least two other first members 120 (e.g., at least one diamond). In some embodiments, the length of at least one first end unjoined portion 123 of a first member 120 is sufficient to cross at least three other first members 120 (e.g., at least four other first members 120, at least five other first members 120, at least six other first members 120, etc.), which equates to at least two diamonds (e.g., at least three diamonds, at least four diamonds, at least five diamonds, etc.). In one or more embodiments, the terminal end of at least one overlap portion 125 of a second member 124 is not greater than eight diamonds (e.g., not greater than six diamonds, not greater than four diamonds, etc.) from a first end bent portion 122.

Figure 3B:
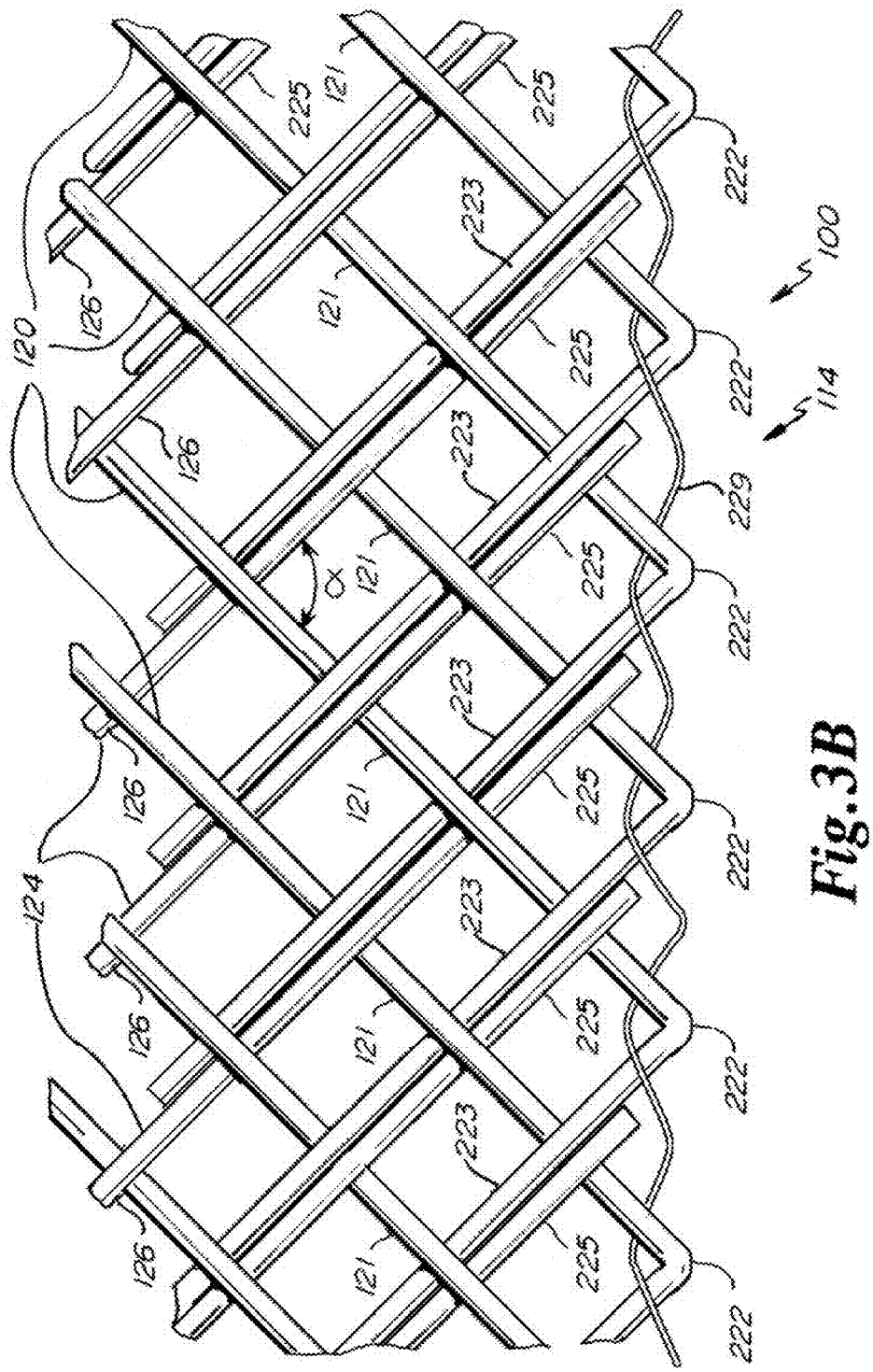
FIG. 3B depicts an enlarged portion of the second end of the woven stent of FIG. 2 in accordance with at least one embodiment of the present disclosure.

As shown in FIG. 3B, in one or more embodiments of the present disclosure, stent 100 may include first members 120 that include a second end unjoined portion 223 extending in the second helical direction around the central axis A and a second end bent portion 222 connecting the first body portion 121 to the second end unjoined portion 223 at the second end 114. Stent 100 may also include second members 124 that include a second end overlap portion 225 extending from the second body portion 126 and extending alongside the second end unjoined portion 223 of a first member 120.

Figure 3C:
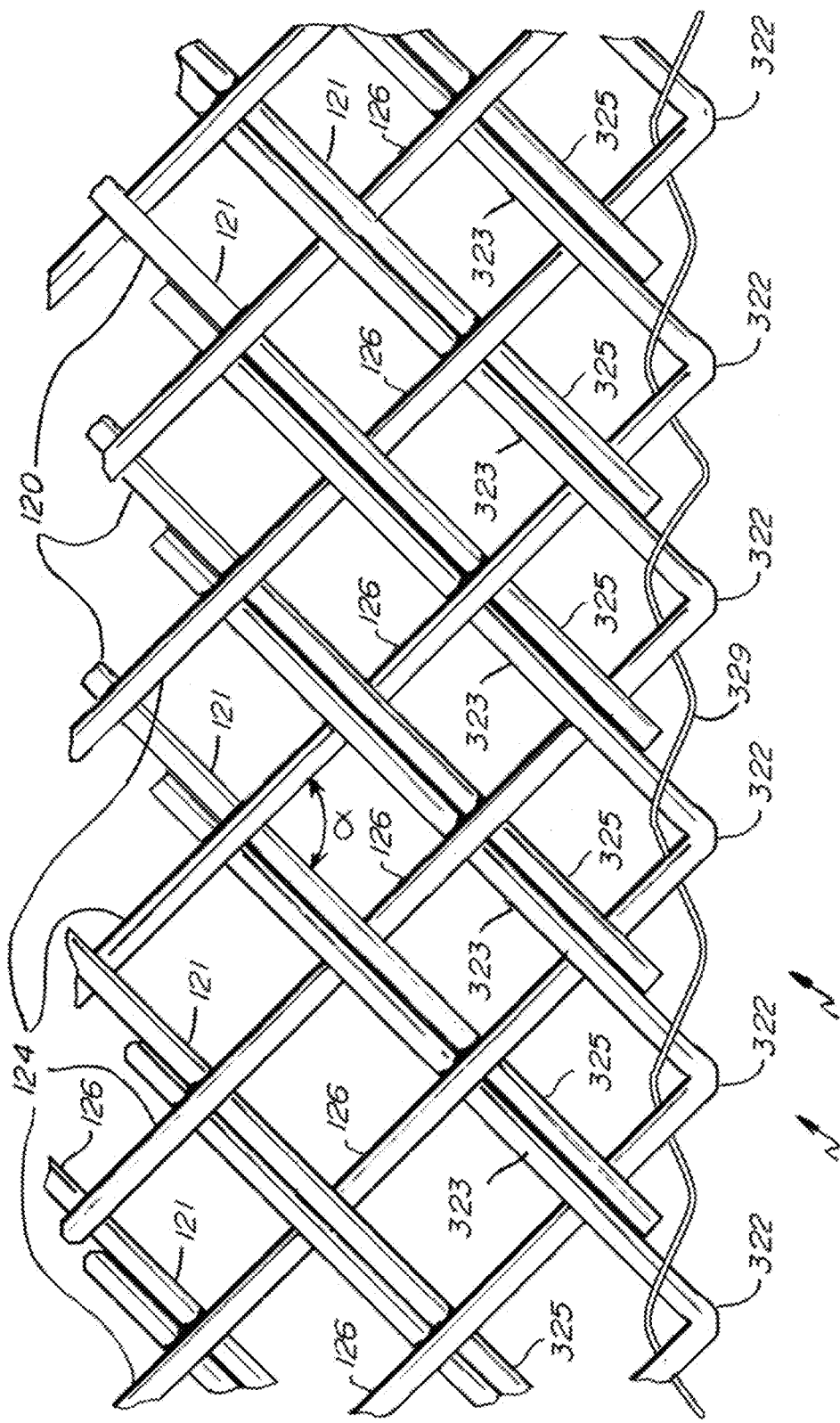
FIG. 3C depicts an enlarged portion of the second end of the woven stent of FIG. 2 in accordance with at least one embodiment of the present disclosure.

In FIGS. 3A and 3B, the first members include both first end bent portions and second end bent portions and both first end unjoined portions and second end unjoined portions. In an alternative embodiment shown in FIG. 3C, one or more of the second members 124 may include a second end bent portion 322 and a second end unjoined portion 323 extending in the first helical direction around the central axis A, the second end unjoined portion 323 corresponding with a second end overlap portion 325 (of one or more corresponding first members 124) extending in the first helical direction. In FIG. 3C, each of the second members 124 includes a second end bent portion 322 and a second end unjoined portion 323 and each of the first members 120 includes a second end overlap portion 325 extending from the first body portion 121.

In one or more embodiments, stent 100 includes a coating 128 (e.g., a second end coating) that encapsulates the second end unjoined portions 223 of the first members 120 and the second end overlap portions 225 of the second members 124 (see FIG. 3B). In one or more embodiments, stent 100 includes a coating 128 (e.g., a second end coating) that encapsulates the second end unjoined portions 323 of the second members 124 and the second end overlap portions 325 of the first members 120 (see FIG. 3C). In one or more embodiments, coating 128 includes both a first end coating and a second end coating (e.g., encapsulating the unjoined portions and overlap portions proximal to the first end and encapsulating the unjoined portions and the overlap portions proximal to the second end). In one or more embodiments, coating 128 includes two discontinuous coatings, wherein at least a portion of a medial portion between the first end 112 and the second end 114 is not coated. In one or more embodiments, coating 128 extends from the first end 112 to the second end 114. In one or more embodiments, coating 128 extends beyond one or both of the first end bent portions 122 and the second end bent portions 222.

A coating 128 of the present disclosure may have any suitable thickness provided that the coating encapsulates the first end unjoined portions 123 of the first members 120 and the first end overlap portions 125 of the second members 124. In one or more embodiments, coating 128 may have any suitable thickness provided that the coating encapsulates the second end unjoined portions 223, 323 and the second end overlap portions 225, 325. A coating of the present disclosure may provide a positional stability to the members and may eliminate or reduce the likelihood of an unjoined portion 123, 223, 323 or an overlap portion 125, 225, 325 becoming unbraided, which would result in a loose end (e.g., a protruding loose end). In one or more embodiments, at least one of the first end unjoined portions 123 of the first members 120 is not joined (e.g., bonded, adhered, fixed, etc.) with a corresponding first end overlap portion 125 of a second member 124 in the absence of coating 128. Similarly, in one or more embodiments, at least one of the second end unjoined portions 223, 323 is not joined with a corresponding second end overlap portion 225, 325 in the absence of coating 128.

In one or more embodiments, at least one of the first end 112 and the second end 114 is a closed loop atraumatic end, wherein the closed loop is a cell formed at least in part by a first end bent portion 122 or a second end bent portion 222, 322. In one or more embodiments, stent 100 may include a suture 129, 229, 329 (or other longitudinal article such as a wire, etc.) woven through at least one cell formed in part by a first or second end bent portion, as shown in FIGS. 3A-3C. In the present disclosure, a suture 129, 229, 329 woven through at least one cell may allow an operator (e.g., a physician, etc.) to retrieve stent 100 that has been delivered and/or deployed at an implantation site.

Figure 4A:
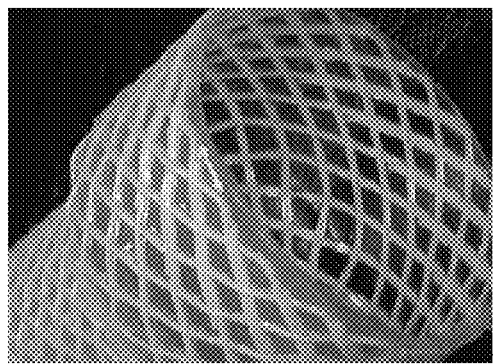
FIG. 4A shows a perspective view of an end of a woven stent in accordance with at least one embodiment of the present disclosure.

FIG. 4A shows a perspective view of a stent 100 according to one or more embodiments described herein. Stent 100 of FIG. 4A includes a coating 128 that extends in the longitudinal direction beyond all of the first end bent portions of first members. FIG. 4A shows a three-diamond snip length of the first end unjoined portions, which extend alongside corresponding overlap portions of second members. Also depicted in FIG. 4A is a cylindrical first end 112 having a first end diameter and a cylindrical medial portion 118 having a medial diameter that is smaller than the first end diameter.

Figure 4B:
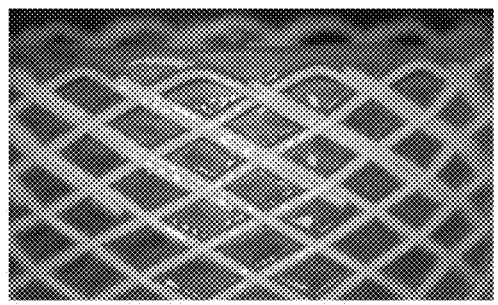
FIG. 4B shows a side view of an end of a woven stent in accordance with at least one embodiment of the present disclosure.

FIG. 4B shows a side view of a stent 100 according to one or more embodiments described herein. Stent 100 of FIG. 4B includes a coating 128 that extends in the longitudinal direction beyond all of the first end bent portions of first members. FIG. 4B shows a three-diamond snip length of the first end unjoined portions, which extend alongside corresponding overlap portions of second members.

Figure 4C:
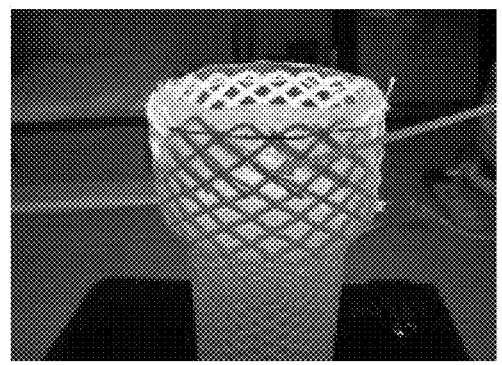
FIG. 4C shows a perspective view of an end of a woven stent in accordance with at least one embodiment of the present disclosure wherein an unjoined portion is shown to have slipped.

In the event that an unjoined portion or an overlap portion partially unravels from the braided configuration or slips out of position due to an applied force (e.g., pulling a suture secured to a first or second stent end), the coating 128 of the present disclosure may provide an improved ability to secure the unjoined portions and/or the overlap portions such that none of the unjoined portions (e.g., first end unjoined portions 123, second end unjoined portions 223, 323) protrudes outside the coating and none of the overlap portions (e.g., first end overlap portions 125, second end overlap portions 225, 325) protrudes outside the coating. For example, FIG. 4C shows a perspective view of a stent 100 having a three-diamond snip length of the first end unjoined portions, which extend alongside corresponding overlap portions of second members. Also depicted in FIG. 4C is a cylindrical first end 112 having a first end diameter and a cylindrical medial portion 118 having a medial diameter that is smaller than the first end diameter. Also shown in FIG. 4C is a suture 129 woven through a plurality of cells formed at least in part by first end bent portions. As shown in FIG. 4C, due to a tensile force applied to suture 129, a first end unjoined portion slipped out of the over-under braid pattern, but the coating did not allow the unjoined portion to protrude outside of the silicone coating 128 and kept the loop end intact and otherwise unraveled.

One or more aspects of the present disclosure relates to a method for manufacturing a stent 100 as discussed herein. The method includes forming a tubular structure 110, as previously described, having a first end 112 and a second end 114, wherein the tubular structure 110 defines a lumen 116, as previously described, extending from the first end 112 to the second end 114 and defines a central axis A, as previously described, extending through the lumen 116 in a longitudinal direction of the tubular structure 110.

In one or more embodiments, forming the tubular structure 110 includes braiding a plurality of first members 120 with a plurality of second members 124 to form a braided configuration. Any of a wide variety of braided configurations may be used and may be selected based on, for example, the intended application and implantation site of stent 100.

In at least one embodiments, forming the tubular structure 110 includes bending at least one of the plurality of first members 120 to form a first end bent portion 122 connecting a first body portion 121 arranged to extend in a first helical direction to a first end unjoined portion 123 at the first end 112. As shown in FIG. 3A, bent portion 122 is disposed at or near the first end 112. In some embodiments, the first end unjoined portion 123 is arranged to extend in a second helical direction around the central axis A, wherein the second helical direction is opposite of the first helical direction. Herein, "opposite" of a particular helical direction is used to refer to the handedness of the helical direction. Thus, the opposite of a left-handed helical direction is a right-handed helical direction. A helical direction may or may not have the same pitch as an opposite helical direction.

In one or more embodiments, forming the tubular structure 110 includes disposing at least one of the plurality of second members 124 such that the second member 124 includes a first end overlap portion 125 extending alongside the first end unjoined portion 123 of a first member 120 and such that a second body portion 126 extends from the first end overlap portion 125 in the second helical direction around the central axis A and toward the second end 114.

In one or more embodiments, the position of the unjoined portions (e.g., first end unjoined portions 123, second end unjoined portions 223, 323) and the overlap portions (e.g., first end overlap portions 125, second end overlap portions 225, 325) may be secured. For example, in the present disclosure, unjoined portions and overlap portions may be secured by applying a coating to encapsulate the unjoined portions and overlap portions and curing the coating. As described hereinbelow, an unjoined portion may be laser joined or ultrasonic joined to an overlap portion in order to secure the position thereof (e.g., to avoid unraveling, to reduce or eliminate loose ends, etc.).

In one or more embodiments, coating may include coating at least a portion of the first end such that the coating encapsulates the first end unjoined portion of at least one first member and the first end overlap portion of at least one second member. In one or more embodiments, coating may include coating at least a portion of the second end such that the coating encapsulates the second end unjoined portions and the second end overlap portions. In some embodiments, coating may include coating both the first end and the second end. In some embodiments, coating may include coating the entire tubular structure. In some embodiments, coating may include applying more than one coating (e.g., two coatings of the same material, two coatings of different materials, etc.).

Coating may be performed using any of a wide variety of coating techniques including, but not limited to, spraying, dipping, applying with a brush, and other techniques.

In one or more embodiments, securing an unjoined portion and an overlap portion may include directing laser or ultrasonic energy to heat the unjoined portion (e.g., a first end unjoined portion) and the overlap portion (e.g., the first end overlap portion) to a joining temperature for a time sufficient to form a bond upon cooling and allowing the unjoined portion and the overlap portion to cool, thereby forming a bond between the unjoined portion and the overlap portion. In one or more embodiments directing the laser or ultrasonic energy and allowing the portions to cool may occur before the coating of at least a portion of the tubular structure (e.g., the first end, the second end, etc.).

Figure 5:
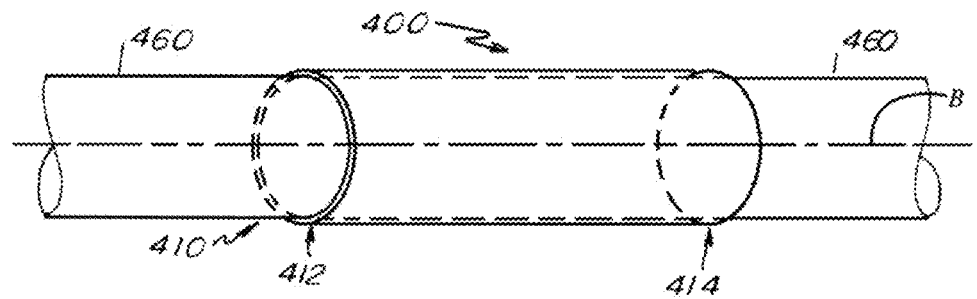
FIG. 5 depicts a schematic of a stent according to at least one embodiment the present disclosure, wherein the stent is disposed on a mandrel.

With reference to FIG. 5, one or more aspects of the present disclosure relates to a method for manufacturing a stent 400. In one or more embodiments, the method includes concentrated energy (e.g., a laser, ultrasonic energy, etc.) to bond or weld (e.g., seam weld) polymeric filaments in order to form, for example, a loop-formed, atraumatic end on a braided stent made from one or more of polyethylene terephthalate (PET) filaments, bioabsorbable polymeric filaments (e.g., polylactic acid (PLA), polyglycolic acid (PGA), etc.), and a combination of both or any suitable bioabsorbable polymer.

Figure 6:
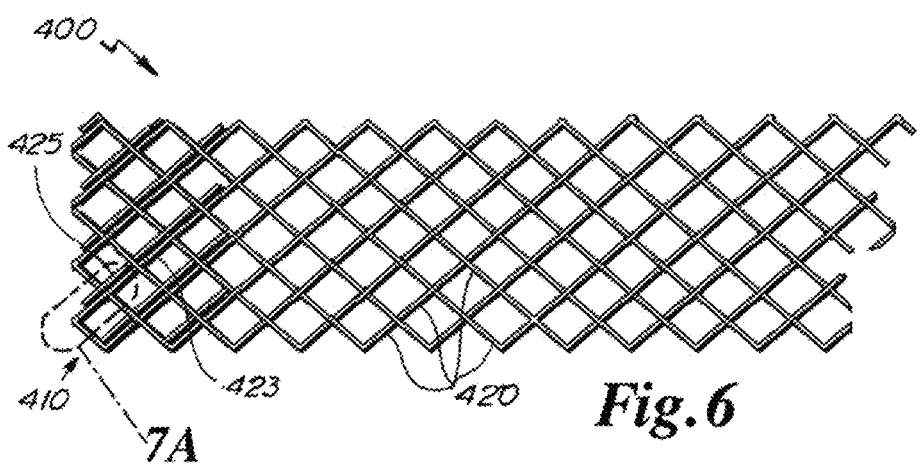
FIG. 6 depicts a schematic of a stent of FIG. 5 showing additional detail regarding first end unjoined portions of first members and first end overlap portions of second members in accordance with at least one embodiment of the present disclosure.

The method includes forming a tubular structure 410 having a first end 412 and a second end 414. The tubular structure 410 also defines a lumen 416 extending from the first end 412 to the second end 414. The tubular structure may also define a central axis B extending through the lumen 416. With reference to FIG. 6, the tubular structure 410 includes at least one member 420 (e.g., a polymeric filament). In one or more embodiments, the at least one member 420 includes a plurality of members (e.g., at least two members, at least four members, at least 6 members, at least 12 members, at least 18 members, at least 24 members, at least 36 members, etc.).

In the present disclosure, forming the tubular structure 410 may include braiding a plurality of first and second members (e.g., filaments) on a mandrel 460. Forming the tubular structure may be performed using any of a wide variety of methods known in the art, provided that at least one first end unjoined portion is arranged proximal to at least one first end overlap portion, as discussed below.

With reference to FIG. 6, the method may include contacting a first end unjoined portion 423 of the first member 420 with a first end overlap portion 425 of the second member 420. In FIG. 6, the first end overlap portion 423 is parallel to the first end unjoined portion 425.

Figures 7A, 7B:
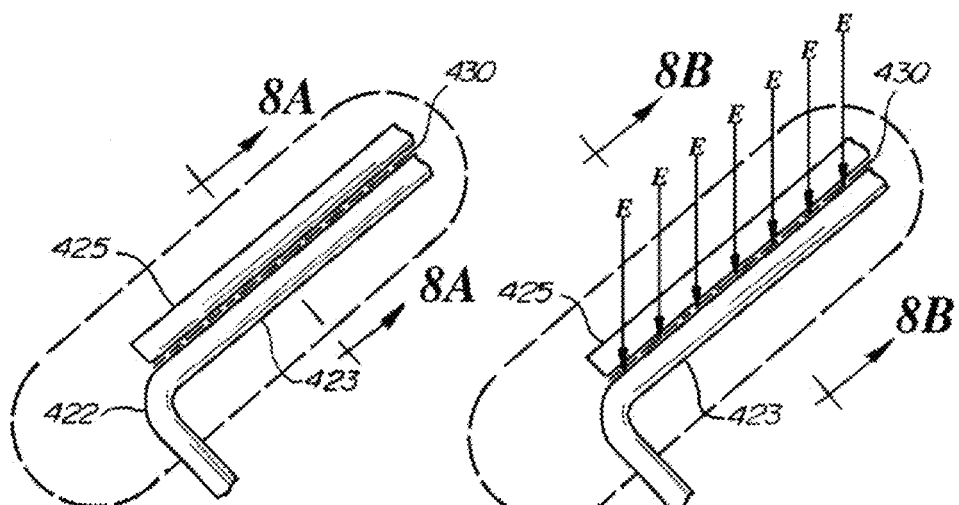
FIG. 7A depicts a schematic showing an enlarged view of a portion of a stent showing positioning of a first end unjoined portion of a first member and a first end overlap portion of a second member in accordance with at least one embodiment of the present disclosure.
FIG. 7B depicts a schematic showing the portion of a stent depicted in FIG. 7A with energy directed toward the first end unjoined portion and the first end overlap portion in accordance with at least one embodiment of the present disclosure.

FIG. 7A shown an enlarged view of a first end unjoined portion 423 and a first end overlap portion 425 of the at least one member 420. For clarity and simplicity, FIG. 7A does not show the first members intersecting with the first end unjoined portion 423 and the first end overlap portion 425.

Figures 8A, 8B:
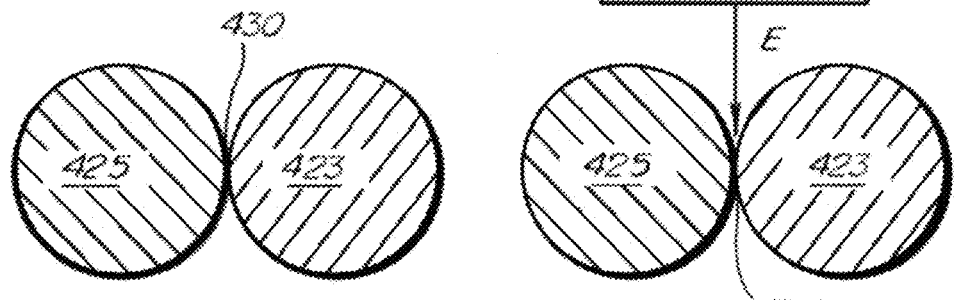
FIG. 8A depicts a schematic of the cross section indicated in FIG. 7A showing a first end unjoined portion and a first end overlap portion in accordance with at least one embodiment of the present disclosure.
FIG. 8B depicts a schematic of the cross section indicated in FIG. 7B showing a first end unjoined portion and a first end overlap portion while directing energy therebetween in accordance with at least one embodiment of the present disclosure.

FIG. 7A shows that a line of contact 430 (shown as dashed line) is formed between the first end unjoined portion 423 and the first end overlap portion 425 when the first end unjoined portion 423 and the first end overlap portion 425 are contacted in a generally parallel configuration. FIG. 8A shows a schematic of a cross-section of the members of FIG. 7A. Notably, the line of contact 430 is shown as a point of tangency between the first end unjoined portion 423 and the first end overlap portion 425.

The method includes joining the first end unjoined portion 423 and the first end overlap portion 425, thereby forming a bond between the first end unjoined portion 423 and the first end overlap portion 425. With reference to FIG. 7B, in one or more embodiments, joining may include directing energy E (e.g., laser energy, ultrasonic energy, etc.) at the line of contact such that the directed energy is absorbed by the first end unjoined portion 423 and the first end overlap portion 425. Directing the energy at the line of contact may include successively directing energy at points along the line of contact. In one or more embodiments, joining may include directing energy E (laser energy, ultrasonic energy, etc.) toward a connecting material (e.g., a radiopaque connecting material), that includes a radiopaque component and a thermoplastic polymer component, such that the thermoplastic polymer component melts, contacts the first end unjoined portion 423 and the first end overlap portion 425, and cools to form a bond between the first end unjoined portion 423 and the first end overlap portion 425.

With reference to FIG. 7B and FIG. 8B, in one or more embodiments, the absorption of directed energy E from an energy source serves to heat the first end unjoined portion 423 and the first end overlap portions 425 at the line of contact 430 to a joining temperature for a time sufficient to form a bond upon cooling. In one or more embodiments, directing laser energy includes directing a laser beam from a source of laser. In the present disclosure, directing laser energy is meant to include the focused direction of intense energy toward the line of contact between the first end unjoined portion 423 and the first end overlap portion 425. In one or more embodiments, directing laser energy includes heating and melting at least a portion of at least one of the first end unjoined portion 423 and the first end overlap portion 425, preferably while not melting other portions of members extending in a direction parallel to the first end unjoined portion 423 and the first end overlap portion 425.

In one or more embodiments, joining includes allowing the line of contact (e.g., the material at or near the line of contact) to cool to a temperature below a melting temperature of the member.

Figure 7C:
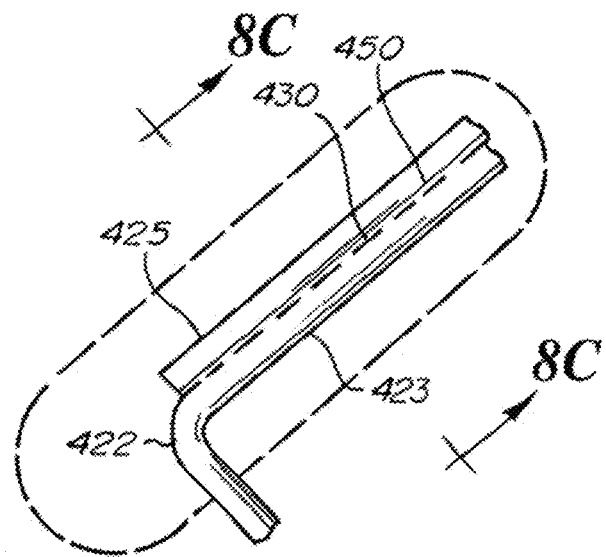
FIG. 7C depicts a schematic showing the portion of a stent depicted in FIG. 7B after the first end unjoined portion and the first end overlap portion are allowed to cool in accordance with at least one embodiment of the present disclosure.
Figure 8C:
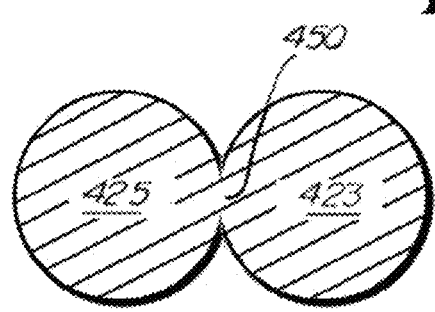
FIG. 8C depicts a schematic of the cross section indicated in FIG. 7C showing a first end unjoined portion bonded to a first end overlap portion in accordance with at least one embodiment of the present disclosure.

With reference to FIG. 7C and FIG. 8C, it can be seen that the first end unjoined portion 423 and the first end overlap portion 425 have been bonded along at least a portion of the line of contact 450. FIG. 8C shows that the first end unjoined portion 423 and the first end overlap portion 425 have combined to form an integral bonded portion (e.g., a weld such as a seam weld). In one or more embodiments, joining the first end unjoined portion 423 and the first end overlap portion 425 includes forming a molecular bond between the first and second members. To achieve a molecular bond, certain chemical characteristics must be met. For example, an ultrasonic frequency may be reached to allow for the member material (e.g., PET, PLA, PGA, etc.) to reach a material melting point (e.g., 255 degrees Celsius for PET, based on differential scanning calorimetry (DSC) testing). However, the frequency may be limited so as to avoid generating a temperature at or above the material degradation temperature (based on thermo gravimetric analysis (TGA) testing) (e.g., 353 degrees Celsius for PET).

In one or more embodiments, each of the unjoined portion and the overlap portion is a terminal end portion (i.e., a portion extending from the terminal end of a second member) of a second member and the joining of the unjoined portion and the overlap portion forms a closed loop at the first end or second end of the tubular structure. In other words at least one of the unjoined portion and the overlap portion extends directly or indirectly from a bent portion 422 at the first end (see FIGS. 7A-7C) or the second end.

Figure 8D:
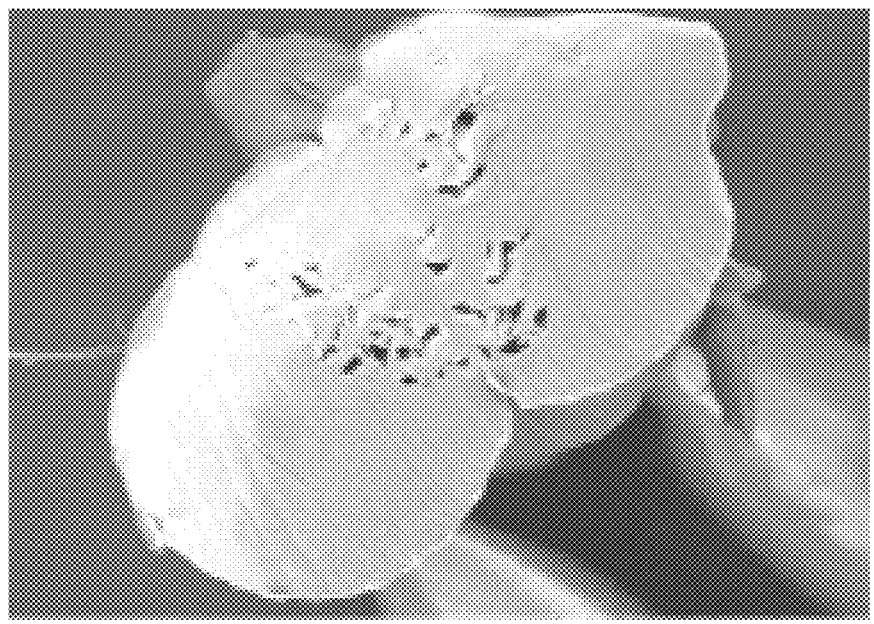
FIG. 8D depicts a perspective view of a cross section of a first end unjoined portion and a first end overlap portion that have been joined in accordance with at least one embodiment of the present disclosure.

FIG. 8D shows a photograph of a cross section of members that were laser welded on a mandrel.

In one or more embodiments, the first members and second members of stent 400 may be formed from any of the wide variety of materials disclosed with reference to first and second members of stent 100. For example, a first member and/or second member may include a thermoplastic and/or bioabsorbable polymer including, but not limited to, polyethylene terephthalate (PET), polylactic acid (PLA), and polyglycolic acid (PGA). Thermoplastic materials may be welded by melting, optionally re-melting, and optionally re-molding. Thermoplastic materials, once formed, may be re-melted and reformed by re-introducing heat and pressure, making this type of material suitable to joining (e.g., laser joining, ultrasonic joining) of the present disclosure.

In the present disclosure, the joining temperature may be in a range of from equal to or greater than a melting temperature of the first and/or second member material of construction to less than a degradation temperature of the first and/or second member material of construction. In the one or more embodiments in which the at least one first and/or second member includes polyethylene terephthalate, the joining temperature may be in a range of from about 255 degrees Celsius to about 353 degrees Celsius.

In one or more embodiments in which a laser source is used to direct a laser beam at the line of contact, the focal spot may be targeted on the work piece surface which will be welded. For example, in FIG. 8B, the focal spot is point along the line of contact between the first end unjoined portion 423 and the first end overlap portion 425. At the surface of the first and/or second members, the large concentration of light energy is converted into thermal energy. The surface of the work piece starts melting and the thermal energy progresses through the surface by surface conductance. In one or more embodiments, the beam energy is maintained such that the temperature of the heated portion of the work piece (e.g., the first and/or second members) is below the vaporization and/or degradation temperature of the work piece material. Use of a large concentration of light energy (e.g., laser) may be advantageous in that the process may be relatively fast, efficient, may require no consumable materials, and will not contaminate the weld zone (e.g., the zone in which first and/or second member material is melted).

Due to the relatively small diameters of the first and/or second members being joined in the present disclosure, the first and/or second members provide a relatively small work surface area to generate a molecular bond using concentrated energy (e.g., laser, ultrasonic, etc.). Also, due to the circular nature of the first and/or second members (e.g., PET, PLA, PGA members), a relatively small point of contact exists between the first and second members (see FIG. 8A, FIG. 9A).

Figure 9A:
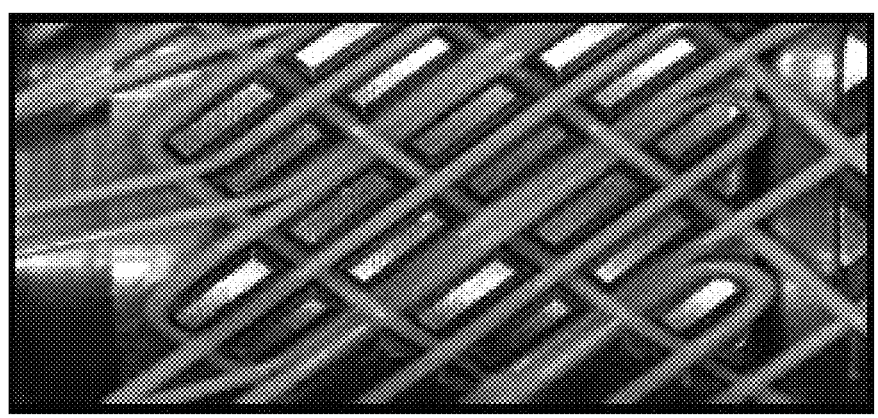
FIG. 9A shows a side view of a plurality of first end unjoined portions to be bonded to first end overlap portions in accordance with at least one embodiment of the present disclosure.

As shown in FIG. 9A, members may be held together on a stent mandrel prior to directing of concentrated energy (e.g., laser, ultrasonic, etc.) for welding. It is useful that the concentrated energy (e.g., laser, ultrasonic, etc.) be accurately and precisely directed into the mandrel geometry relative to the first end unjoined portion of the first member and the first end overlap portion of the second member in a consistent manner and at an appropriate focal length in order to achieve a suitable weld (see FIGS. 7C and 10) upon cooling. In the present disclosure, a suitable weld is one that will produce an acceptable tensile strength result from a shear lap-weld tensile test. Incorrect positioning and/or direction of the concentrated energy (e.g., laser, ultrasonic, etc.) or, for example, operating a laser at an incorrect focal length with the PET members (or PLA members, or PGA members, etc.) within the mandrel geometry, may lead to an insufficient weld strength (i.e., an unacceptable tensile strength result from a shear lap-weld tensile test).

Figure 9B:
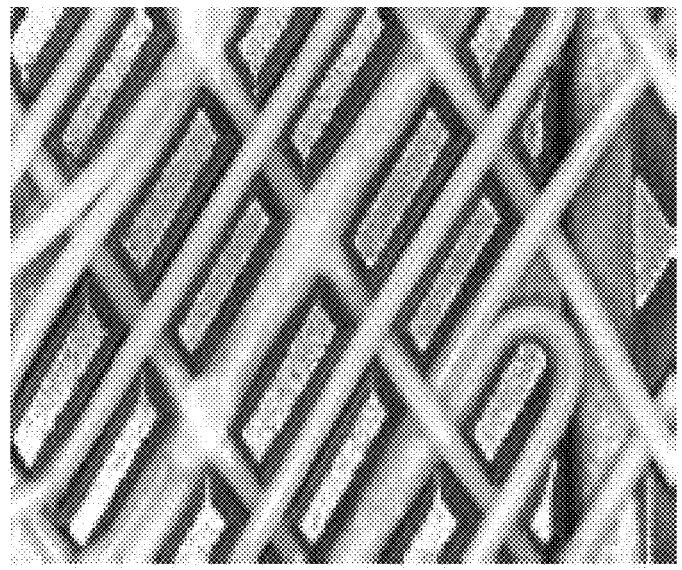
FIG. 9B shows an enlarged view of the members of FIG. 9A after joining several first end unjoined portions to corresponding first end overlap portions in accordance with at least one embodiment of the present disclosure.

FIG. 9B shows a portion of the first and second members of FIG. 9A after utilizing laser welding to join first and second members in at least three locations.

Figure 9C:
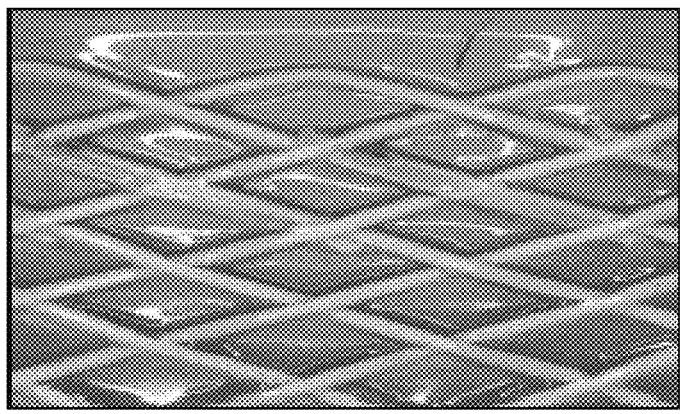
FIG. 9C shows a stent having an end including a plurality of first end unjoined portions, each joined to a corresponding first end overlap portion, thereby forming closed-loop joined ends in a stent in accordance with at least one embodiment of the present disclosure.

FIG. 9C shows a plurality of first end unjoined portions, each joined to a corresponding first end overlap portion, forming closed-loop joined ends in a stent. The length of the joined portions in FIG. 9C is two full diamonds.

Figure 10:
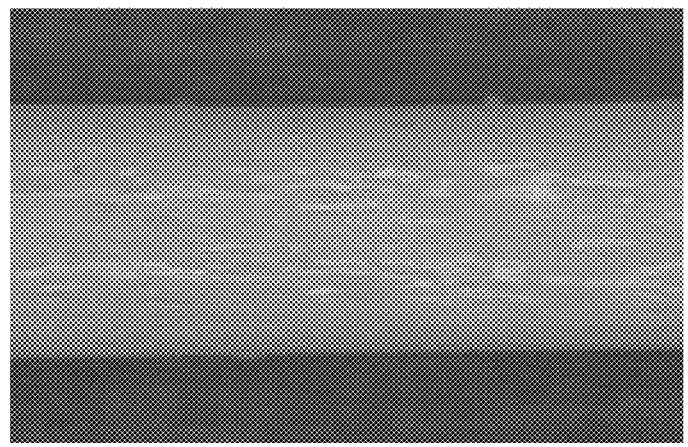
FIG. 10 shows an image of joined first end unjoined portion and first end overlap portion in accordance with at least one embodiment of the present disclosure.

FIG. 10 shows an image of joined first and second members after a laser was used to join the first and second members.

Figure 11:
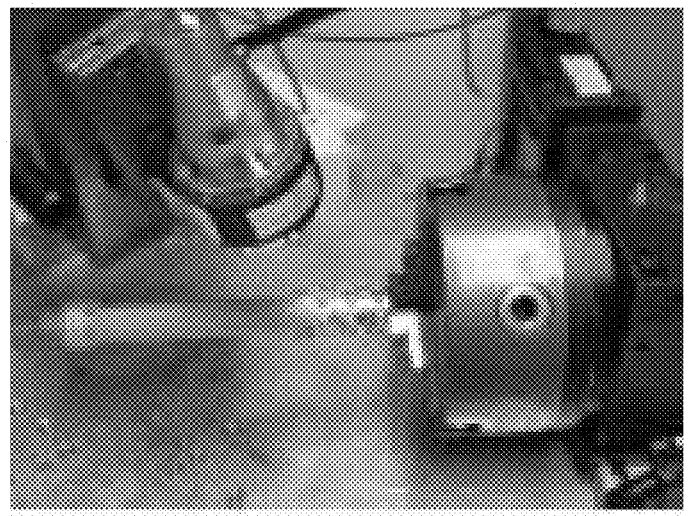
FIG. 11 shows a perspective view of an exemplary set-up including a laser directed toward filaments on a mandrel.

FIG. 11 shows an exemplary set-up including a laser directed toward PET members on a mandrel (anvil).

In one or more embodiments, automated equipment (e.g., high-precision automated equipment) may be useful in the methods of the present disclosure in a manufacturing environment. Automation of the directing of concentrated energy (e.g., laser energy, ultrasonic energy) may provide consistent and repeatable positioning of the laser, relative to the first and/or second member material, and the ability to produce acceptable welding (joining) of the first and/or second member strands (e.g., PET, PLA, PGA strands, etc.). In one or more embodiments, the methods of the present disclosure provide a relatively strong homogenous bond between the first end unjoined portion and the first end overlap portion. In one or more embodiments in which laser energy is utilized, the bond strength may be varied by controlling or varying one or more following parameters: laser power, time, and spot size.

In one or more embodiments, utilization of concentrated light energy (e.g., laser) may be useful due to a combination of low manufacturing costs (e.g., combination of capital outlay and relatively low manufacturing running costs) coupled with enhanced process capability and stability. In at least some embodiments, laser joining may be employed with any of a wide variety of thermoplastic stents and design configurations.

In one or more embodiments, method of manufacturing a stent including laser-joined portions (e.g., unjoined portions, overlap portions) may include coating the laser-joined portions (e.g., unjoined portions, overlap portions). Coating the portions may include encapsulating the portions.

EXAMPLES

Example 1

Unjoined Stent Manufacturing and Testing

Fifteen unjoined woven looped end stents were successfully and repeatedly manufactured and evaluated in a suture tensile test and a peristaltic test.

The fifteen stents were formed by braiding a wire stent using either 36 wires or 24 wires on a mandrel using an over-under pattern. Then, each of the wire stents was loop formed to form a closed loop stent. The snipping distance was three diamonds for all 15 stents. In other words, the distance from the terminal end of the unjoined portion to the terminal end of a corresponding overlap portion was at least three full cells. Each stent was annealed on the mandrel at 190 degrees Celsius for 30 minutes.

All fifteen stents were successfully removed from the mandrel with loop ends intact as per post weld inspection criteria (i.e., no separation of wires). In other words, the woven unjoined portions and overlap portions were intact pre-coating.

Then the fifteen unjoined stents were successfully coated with a silicone coating providing structural support to the weave design.

All fifteen stents successfully passed a post-coating inspection per standard inspection (i.e., no wires protruding through silicone coating, no wire separation, no wire breakage). In other words, the woven unjoined portions and overlap portions of all 15 stents were intact post-coating.

Then, for each stent, a suture was woven through each cell formed at least in part by a first end bent portion. A tensile force was applied to the suture (until suture break) to determine whether the loop ends would remain intact. Each stent was inspected to identify any wire breaks (e.g., wire separation, wire protruding through coating, loop breakage). A maximum of three breaks was allowed. All fifteen stents passed this test. The suture tensile force at suture failure for each of the fifteen stents exceeded 4.0 lbf.

Each of FIGS. 4A and 4B shows one exemplary stent in which all wires and loop ends remained intact.

Upon completion of suture tensile testing, five stents were also tested for peristaltic fatigue to replicate product endurance in an esophagus for approximately 6 months. All stents met or exceeded acceptance criteria. All five stents showed zero loop separation in a pre-fatigue test and zero loop separation in a post-fatigue test, thereby passing the evaluation.

Example 2

Testing of Laser-joined Filaments

Shear lap-weld tensile strength testing was conducted on 17 samples of PET filaments joined by laser at a uniform laser power, time, and spot size. The following results were achieved:

Each stent was evaluated for its ability to maintain the lap weld under a tensile shear stress caused by a tensile load of 4.0 lbf. Each of the seventeen stents met or exceeded acceptance criteria indicating sufficient strength to satisfy the purpose of the design intent of each stent.

A description of some exemplary embodiments of the present disclosure can be contained in the following numbered statements:

Statement 1. A woven stent comprising:
a tubular structure having a first end and a second end, wherein the tubular structure defines a lumen extending from the first end to the second end and defines a central axis extending through the lumen in a longitudinal direction of the tubular structure, and wherein the tubular structure comprises:
a plurality of first members;
a plurality of second members;
wherein the first members and the second members form a braided configuration;
wherein each of the first members comprises:
a first body portion extending in a first helical direction around the central axis;
a first end unjoined portion extending in a second helical direction around the central axis, wherein the second helical direction is opposite of the first helical direction; and
a first end bent portion connecting the body portion to the first end unjoined portion at the first end;
wherein each of the second members comprises:
a first end overlap portion extending alongside the first end unjoined portion of a first member; and
a second body portion extending from the first end overlap portion in the second helical direction around the central axis toward the second end; and
a coating that encapsulates the first end unjoined portions of the first members and the first end overlap portions of the second members.

Statement 2. The woven stent of statement 1 wherein each of the first members further comprises:
a second end unjoined portion extending in the second helical direction around the central axis; and
a second end bent portion connecting the first body portion to the second end unjoined portion at the second end;
wherein each of the second members further comprises a second end overlap portion extending from the second body portion and extending alongside the second end unjoined portion of a first member; and
wherein the woven stent further comprises a second end coating that encapsulates the second end unjoined portions of the first members and the second end overlap portions of the second members.

Statement 3. The woven stent of statement 1 wherein each of the second members further comprises:
a second end unjoined portion extending in the first helical direction around the central axis; and
a second end bent portion connecting the second body portion to the second end unjoined portion at the second end;
wherein each of the first members further comprises a second end overlap portion extending from the first body portion and extending alongside the second end unjoined portion of a second member; and
wherein the woven stent further comprises a second end coating that encapsulates the second end unjoined portions of the second members and the second end overlap portions of the first members.

Statement 4. The woven stent of any of statements 1-3 wherein each of the first and second members is selected from the group consisting of a wire and a filament.

Statement 5. The woven stent of statement 4 wherein the filament comprises a thermoplastic.

Statement 6. The woven stent of statement 4 wherein the filament comprises a bioabsorbable polymer.

Statement 7. The woven stent of any of statements 1-6 wherein the coating comprises silicone.

Statement 8. The woven stent of any of statements 1-7 wherein the coating comprises a bioabsorbable coating.

Statement 9. The woven stent of any of statements 1-8 further comprising a suture woven through at least one cell formed in part by a first end bent portion.

Statement 10. The woven stent of any of statements 1-9 wherein the plurality of first members comprises 18 wires or 18 filaments and the plurality of second members comprises 18 wires or 18 filaments.

Statement 11. The woven stent of any of statements 1-10 wherein, in the absence of the coating, each of the first end unjoined portions of the first members is not joined with a corresponding first end overlap portion of a second member.

Statement 12. A method for manufacturing a stent, the method comprising:
forming a tubular structure having a first end and a second end, wherein the tubular structure defines a lumen extending from the first end to the second end and defines a central axis extending through the lumen in a longitudinal direction of the tubular structure, and wherein forming the tubular structure comprises:
braiding a plurality of first members with a plurality of second members to form a braided configuration such that each of the first members comprises:
bending at least one of the plurality of first members to form a first end bent portion connecting a first body portion arranged to extend in a first helical direction to a first end unjoined portion at the first end; the first end unjoined portion arranged to extend in a second helical direction around the central axis, wherein the second helical direction is opposite of the first helical direction; and
disposing at least one of the plurality of second members such that the second member includes a first end overlap portion extending alongside the first end unjoined portion of a first member and such that a second body portion extends from the first end overlap portion in the second helical direction around the central axis and toward the second end; and
coating at least a portion of the first end such that the coating encapsulates the first end unjoined portion of the at least one first member and the first end overlap portion of the at least one second member.

Statement 13. The method of statement 12 further comprising:
directing laser or ultrasonic energy to heat the first end unjoined portion and the first end overlap portion to a joining temperature for a time sufficient to form a bond upon cooling; and
allowing the first end unjoined portion and the first end overlap portion to cool, thereby forming a bond between the first end unjoined portion and the first end overlap portion;
wherein directing laser or ultrasonic energy and allowing the first end unjoined portion and the first end overlap portion to cool occur before coating at least a portion of the first end.

Statement 14. A method for manufacturing a stent, the method comprising:

forming a tubular structure having a first end and a second end, wherein the tubular structure defines a lumen extending from the first end to the second end, and wherein the tubular structure comprises a plurality of first members and a plurality of second members;

contacting a first end unjoined portion of a first member with a first end overlap portion of a second member, wherein the first end overlap portion is parallel to the first end unjoined portion and wherein a line of contact is formed between the first end unjoined portion and the first end overlap portion; and joining the first end unjoined portion and the first end overlap portion, wherein joining comprises:
   directing laser or ultrasonic energy at the line of contact to heat the first end unjoined portion and the first end overlap portion at the line of contact to a joining temperature for a time sufficient to form a bond upon cooling; and
   allowing the line of contact to cool, thereby forming a bond between the first end unjoined portion and the first end overlap portion.

Statement 15. The method of statement 14 wherein directing laser or ultrasonic energy comprises using a laser.

Statement 16. The method of statement 14 or statement 15 wherein at least one of the plurality of first members and one of the plurality of second members comprises a thermoplastic polymer.

Statement 17. The method of statement 16 wherein the thermoplastic polymer is polyethylene terephthalate.

Statement 18. The method of statement 17 wherein the joining temperature is in a range of from about 255 degrees Celsius to about 353 degrees Celsius.

Statement 19. The method of any of statements 14-18 wherein at least one of the plurality of first members and one of the plurality of second members comprises a bioabsorbable polymer.

Statement 20. The method of any of statements 12-19 wherein the joining temperature is equal to or greater than a melting point of the first end unjoined portion or the first end overlap portion and less than the degradation point of the first end unjoined portion or the first end overlap portion.

Statement 21. The method of any of statements 12-20 wherein forming the tubular structure comprises braiding a plurality of first members with a plurality of second members on a mandrel.

Statement 22. The method of any of statements 12-21 wherein wherein each of the first end unjoined portion and the first end overlap portion is a terminal end portion of a first member or second member and the joining of the first end overlap portion and the first end overlap portion forms a closed loop at the first end of the tubular structure.

Statement 23. The method of any of statements 12-22 further comprising coating at least a portion of the first end such that the coating encapsulates the first end unjoined portions of the first members and the first end overlap portions of the second members.

The above disclosure is intended to be illustrative and not exhaustive. This description will suggest many variations and alternatives to a person of ordinary skill in this art. The various elements shown in the individual figures and described above can be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the detailed description. Those skilled in the art can recognize other equivalents to the specific embodiment described herein which equivalents are intended to be encompassed by the claims attached hereto.

The invention claimed is:

1. A method for manufacturing a stent, the method comprising:
   forming a tubular structure having a first end and a second end, wherein the tubular structure defines a lumen extending from the first end to the second end and defines a central axis extending through the lumen in a longitudinal direction of the tubular structure, and wherein forming the tubular structure comprises:
      braiding a plurality of first members with a plurality of second members to form a braided configuration having a plurality of crossover points;
      bending at least one of the plurality of first members to form a first end bent portion connecting a first body portion arranged to extend in a first helical direction to a first end unjoined portion at the first end; the first end unjoined portion arranged to extend in a second helical direction around the central axis, wherein the second helical direction is opposite of the first helical direction; and
      disposing at least one of the plurality of second members such that the second member includes a first end overlap portion extending alongside the first end unjoined portion of a first member and such that a second body portion extends from the first end overlap portion in the second helical direction around the central axis and toward the second end, wherein the first end overlap portion of the second member and the first end unjoined portion of the first member both extend across at least one crossover point with another first or second member; and
   coating at least a portion of the first end such that the coating encapsulates the first end unjoined portion of the at least one first member and the first end overlap portion of the at least one second member.

2. The method of claim 1 further comprising:
   directing laser or ultrasonic energy to heat the first end unjoined portion and the first end overlap portion to a joining temperature for a time sufficient to form a bond upon cooling; and
   allowing the first end unjoined portion and the first end overlap portion to cool, thereby forming a bond between the first end unjoined portion and the first end overlap portion;

wherein directing laser or ultrasonic energy and allowing the first end unjoined portion and the first end overlap portion to cool occur before coating at least a portion of the first end.

3. A method for manufacturing a stent, the method comprising:
   forming a tubular structure having a first end and a second end, wherein the tubular structure defines a lumen extending from the first end to the second end, and wherein the tubular structure comprises a plurality of first members and a plurality of second members interwoven at a plurality of crossover points;
   contacting a first end unjoined portion of a first member with a first end overlap portion of a second member, wherein the first end overlap portion is parallel to the first end unjoined portion and wherein a line of contact is formed between the first end unjoined portion and the first end overlap portion; and
   joining the first end unjoined portion and the first end overlap portion, wherein joining comprises:
      directing laser or ultrasonic energy at the line of contact to heat the first end unjoined portion and the first end overlap portion at the line of contact to a joining temperature for a time sufficient to form a bond upon cooling; and
      allowing the line of contact to cool, thereby forming a bond between the first end unjoined portion and the first end overlap portion;
   wherein the bond extends across at least one crossover point with another first or second member.

4. The method of claim 3 wherein directing laser or ultrasonic energy comprises using a laser.

5. The method of claim 3 wherein at least one of the plurality of first members and one of the plurality of second members comprises a thermoplastic polymer.

6. The method of claim 5 wherein the thermoplastic polymer is polyethylene terephthalate.

7. The method of claim 6 wherein the joining temperature is in a range of from about 255 degrees Celsius to about 353 degrees Celsius.

8. The method of claim 3 wherein the joining temperature is equal to or greater than a melting point of the first end unjoined portion or the first end overlap portion and less than the degradation point of the first end unjoined portion or the first end overlap portion.

9. The method of claim 3 wherein forming the tubular structure comprises braiding a plurality of first members with a plurality of second members on a mandrel.

10. The method of claim 3 wherein each of the first end unjoined portion and the first end overlap portion is a terminal end portion of a first member or second member and the joining of the first end overlap portion and the first end overlap portion forms a closed loop at the first end of the tubular structure.

11. The method of claim 3 further comprising coating at least a portion of the first end such that the coating encapsulates the first end unjoined portions of the first members and the first end overlap portions of the second members.

* * * * *